United States Patent [19]

Winner

[11] Patent Number: Plant 6,063

[45] Date of Patent: Dec. 22, 1987

[54] VARIETY OF GERANIUM NAMED CLARET

[75] Inventor: Blair L. Winner, Lompoc, Calif.

[73] Assignee: Denholm Seeds, Lompoc, Calif.

[21] Appl. No.: 800,807

[22] Filed: Nov. 22, 1985

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Webb, Burden, Robinson & Webb

[57] ABSTRACT

A new geranium cultivar is distinguished by its form, which is abundantly branched from the base with compact growth. The soft green, relatively abundant and small leaves are well placed, giving the appearance of a dense, vigorous growth. The plant flowers profusely, with the moderately sized red, violet accented flowers arranged just above the foliage in a beautifully arranged bouquet.

1 Drawing Figure

BACKGROUND OF THE NEW PLANT

The present invention comprises a new and distinct cultivar of *Pelargonium hortorum* which is a zonal geranium known by the varietal name Claret (Oglevee No. 886 and Denholm No. 42023-1). The new variety was discovered in a selective breeding program by Mr. Blair L. Winner and is a selection from the selfing of "Glacier Crimson" (U.S. Plant Pat. No. 5,057, formerly "Bruni").

The new cultivar was discovered in August of 1982 at Denholm Seeds in Lompoc, Calif., was first asexually reproduced by cuttings by Denholm Seeds at Lompoc, Calif., and has been repeatedly asexually reproduced by cuttings at Oglevee Associates, Inc. in Connellsville, Pa. over a 36 month period. It has also been trial and field tested at Connellsville, Pa. during the summers of 1983, 1984 and 1985. It has been found to retain its distinctive characteristics through successive propagations.

The new cultivar is more vigorous and lighter in color than "Glacier Crimson."

The new cultivar, when grown in a glass greenhouse in Connellsville, Pa. using full sunlight, 60° F. night temperature, 68° F. day temperature and 71° F. vent temperature and grown in a soilless media of constant fertilizer of 275–300 parts per million nitrogen and potassium, has a response time from a rooted cutting to a flowering plant in a 10 cm pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the cultivar. The data which define these characteristics were collected from asexual reproductions carried out by Oglevee Associates, Inc. in Connellsville, Pa. The plant histories were taken on plants blossomed under full light in a greenhouse and color readings were taken indoors under 200 foot candles of cool, white fluorescent light. Color references are primarily to The R.H.S. Colour Chart of The Royal Horticultural Society of London.

THE PLANT

Classification:
- *Botanical.*—*Pelargonium hortorum.*
- *Commercial.*—Zonal geranium.

Form: Bush; short; compact; self-branching without pinch.

Height: 19–22 cm.

Growth: Free branching from base; short internodes.

Strength: Stands upright without artificial support.

Foliage: Stalked leaf attachment; no zoning.

Leaves:
- *Size.*—4–7 cm.
- *Shape.*—Reniform.
- *Margin.*—Crenate.
- *Texture.*—Pubescent; waxy.
- *Color.*—Top: Green group 137B. Bottom: Yellow-green group 144B.
- *Ribs and veins.*—Yellow-green group 144C; palmate.

Petioles: 4–8 cm in length; Yellow-green group 144C.

Stem:
- *Color.*—Yellow-green group 144C.
- *Internodes.*—1.0–1.5 cm in length.

THE BUD

Shape: Upright; hemispherical; cluster.

Size: 3–4 cm across.

INFLORESCENCE

Blooming habit: Umbel of 20–30 florets; continuous; hemispherical in shape; semi-double.

Size: 9–11 cm across.

Borne: 3–6 cm above foliage; umbel; florets on pedicel; pedicels on peduncle.

Florets:
- *Form.*—Round outline 6–9 petals.
- *Color.*—Top: Four petals have purplish eye and veining; color red group 40A; eye color red-purple group 67C; reverse 40D red group.
- *Petals.*—2.4–2.6 cm long; 1.4–2.2 cm wide; smooth margin; palmate venation.
- *Size.*—3.6–4.6 cm long.
- *Texture and appearance.*—Smooth velvet feel; sparkling reflective flecks.

Petaloids:
- *Quantity.*—1–4.

*Shape.—Irregular.*

*Color.*—Front: Red group 40A. Back: Red group 40D.

Pedical:

*Length.*—1.5–2.0 cm in length.

*Color.*—Yellow-green group 145B.

Peduncle: Arise from node opposite leaf petiole; 11–14 cm in length; yellow-green group 144A.

Persistence: Rapid continuous and abundant flowering.

Disease resistance: Moderate resistance to Botrytis flower blight and good resistance to Botrytis and Alternaria leaf spot.

REPRODUCTIVE ORGANS

Stamens anthers: Yellow immature; purplish-brown at maturity.

Filaments: Flat; white at base to bluish red at tip; irregular length.

Pollen: Golden yellow initially; dark brown later.

Pistils:

*Number.*—1 with 5 part stigma.

*Length.*—4 mm.

Stigma: 5 lobed red-purple.

Style: Single; short; off-white; 2–3 mm in length.

Ovaries: 5 mm in length; green; very pubescent (0.1–0.5 mm); superior.

Fruit: None observed.

The new cultivar has superb form, abundantly branched from the base and with compact growth. The soft green, abundant, relatively small leaves are well placed, giving the appearance of dense, vigorous growth. The plant flowers profusely, with the moderately sized red, violet accented flowers arranged just above the foliage in a beautifully arranged bouquet.

The new cultivar has been fingerprinted by Dr. Richard Craig and his associates at Penn State University in State College, Pa. The fingerprinting was conducted on a Waters High Performance Liquid Chromatograph equipped with an automatic injection system, dual pumps, solvent programmer, data module, variable wavelength detector, and a $C_{18}$ column. The anthocyanin and flavonol chemical markers utilizing flower petals as an adjunct for cultivar identification were determined.

The anthocyanin and flavonol concentrations of petals just after anthesis of the cultivar Claret florets sampled in April of 1985 are compared with the cultivar "Glacier Crimson" (U.S. Plant Pat. No. 5,075) and presented below in Tables 1 and 2. Results are based on the average of multiple tests. It should be noted that changes in environment can influence the biosynthesis.

TABLE 1

| | Anthocyanin Concentration ug anthocyanin 3,5 diglucoside/g fresh wt. | | | | | |
|---|---|---|---|---|---|---|
| Cultivar | Delphinidin | Cyanidin | Pelargonidin | Peonidin | Malvidin | Total |
| CLARET | — | 38 | 1959 | 1384 | 83 | 3464 |
| XCR - Bruni | — | 78 | 5251 | 2418 | — | 7747 |

TABLE 2

| | Flavonol Concentration ug/g fresh wt. | | | | | |
|---|---|---|---|---|---|---|
| Cultivar | Qu3-[z] rhagal | Qu3-rut | Qu3-gal | Qu3-glu | Km3-rhagal | Km3-gal |
| CLARET | t | 44 | — | 12 | 255 | 38 |
| XCR - Bruni | 11 | 34 | — | t | 307 | 47 |

| Cultivar | Km3-rut | Km3-xyl | Km3-arab | Km3-rha | Total |
|---|---|---|---|---|---|
| CLARET | 1139 | t | 68 | 166 | 1732 |
| XCR - Bruni | 1257 | 13 | 49 | 185 | 1908 |

[z]Abbreviations:
Km = Kaempferol;
Qu = Quercetin;
arab = arabinoside;
gal = galactoside;
glu = glucoside;
rha = rhamnoside;
rhagal = rhamnosylgalactoside;
rut = rutinoside;
xyl = xyloside.
t = trace < 10 ug.

I claim:

1. A new and distinct variety of geranium plant substantially as herein shown and described and parts therefor.

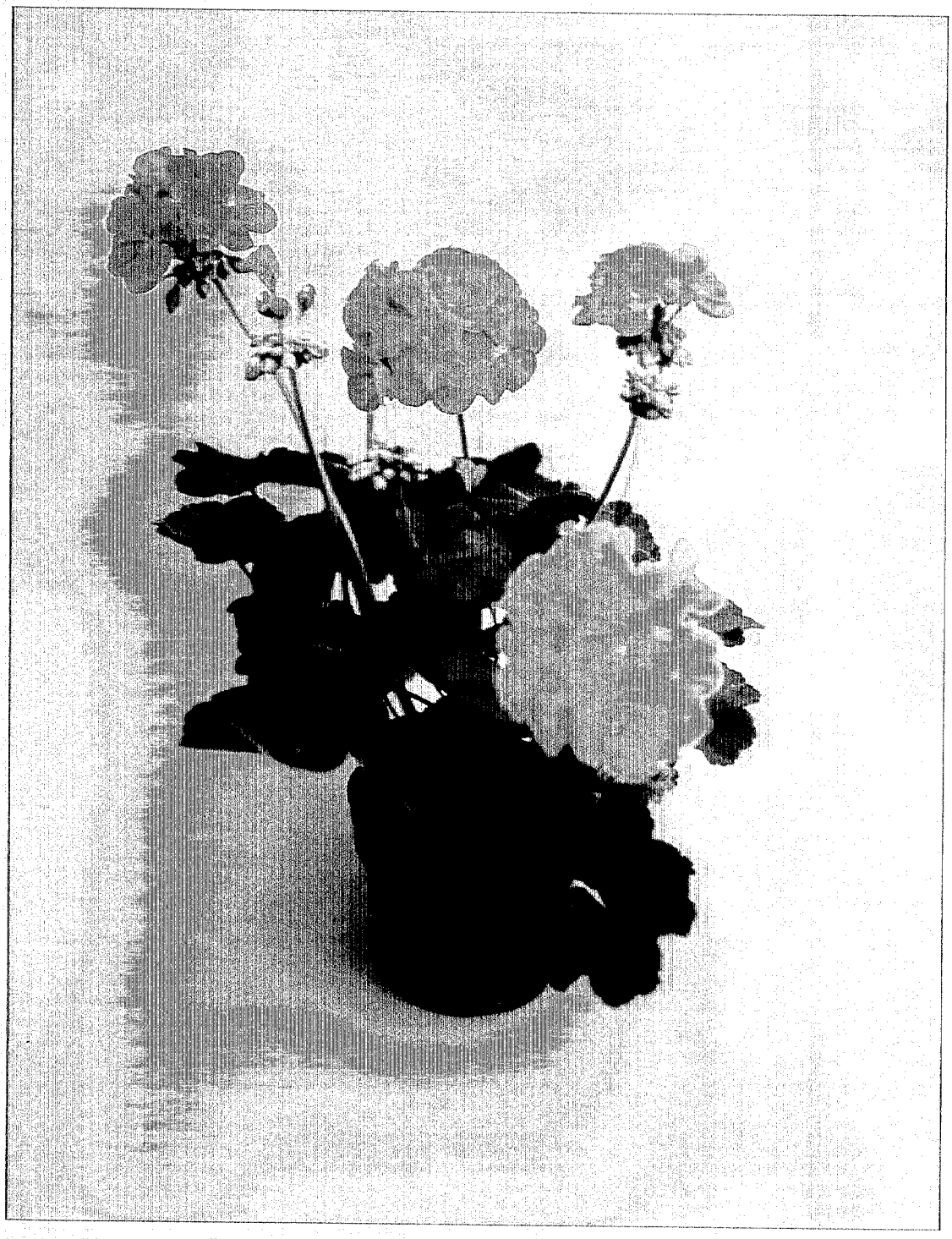

* * * * *